(12) United States Patent
Wilcox et al.

(10) Patent No.: US 7,840,040 B2
(45) Date of Patent: Nov. 23, 2010

(54) METHOD AND APPARATUS FOR CONTROLLING ULTRASOUND IMAGING SYSTEMS HAVING POSITIONABLE TRANSDUCERS

(75) Inventors: Stephen D. Wilcox, Los Gatos, CA (US); Sankaralingam Ramraj, Sunnyvale, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 932 days.

(21) Appl. No.: 11/242,161

(22) Filed: Sep. 30, 2005

(65) Prior Publication Data

US 2007/0078340 A1    Apr. 5, 2007

(51) Int. Cl.
G06K 9/00    (2006.01)
(52) U.S. Cl. ...................................... 382/128
(58) Field of Classification Search ............... 128/916; 382/107; 600/595
See application file for complete search history.

(56) References Cited

U.S. PATENT DOCUMENTS

| | | | |
|---|---|---|---|
| 5,544,654 A | 8/1996 | Murphy et al. | |
| 5,654,509 A | 8/1997 | Miele et al. | |
| 5,876,342 A | 3/1999 | Chen et al. | |
| 5,885,231 A * | 3/1999 | Cramer et al. | 600/595 |
| 5,944,663 A | 8/1999 | Kuth et al. | |
| 6,162,174 A * | 12/2000 | Friemel | 600/447 |
| 6,468,212 B1 | 10/2002 | Scott et al. | |
| 6,599,244 B1 | 7/2003 | Epps et al. | |
| 6,669,633 B2 | 12/2003 | Brodsky et al. | |
| 6,780,154 B2 | 8/2004 | Hunt et al. | |
| 2002/0120192 A1* | 8/2002 | Nolte et al. | 600/424 |
| 2004/0242988 A1* | 12/2004 | Niwa et al. | 600/407 |
| 2004/0249843 A1* | 12/2004 | Damrath | 707/100 |
| 2005/0116935 A1* | 6/2005 | Washburn | 345/167 |
| 2005/0216867 A1* | 9/2005 | Marvit et al. | 715/863 |
| 2005/0256407 A1* | 11/2005 | Hamada | 600/447 |
| 2007/0057911 A1* | 3/2007 | Fateh | 345/156 |

FOREIGN PATENT DOCUMENTS

WO    WO 0186920 A2 *  11/2001
WO    WO 2004066615 A1 *  8/2004

* cited by examiner

*Primary Examiner*—Charles Kim
*Assistant Examiner*—Nirav G Patel

(57) ABSTRACT

A method and system for providing an operational command signal to a workstation of an imaging system. The workstation is provided imaging data from a positionable transducer. The method and system convert at least one of a predetermined plurality of motion patterns imparted by an operator of the system to the transducer into the operational command signal.

15 Claims, 12 Drawing Sheets

| ID | Name | Pictograph | User interface action |
|---|---|---|---|
| | | ↓Z →Y ▭▽12 -13 | |
| 1 | R-L | ▭↗33 | Capture the image and store it in a patient database. |
| 2 | L-R | ◁▭ | Start capturing image data to a movie clip. |
| 3 | R-L-R-L | ▭⋛ | Mouse Right click, bring up a menu. |
| 4 | L-R-L-R | ⋚▭ | Mouse double click, select a user interface object, such as a menu item. |
| 5 | R-L-L-R | ⊲▭⊳ | Invoke an on-screen cursor. |
| 6 | L-R-R-L | ⊲▭⊳ | Select the next measurement in a series of measurements. |
| 7 | D-U | ▭↙ | Mouse left click. |
| 8 | U-D | ▭↖ | Start automatic image gain adjustment. |
| 9 | D-U-D-U | ▭W | Start VCR recording. |
| 10 | U-D-U-D | ▭W | Stop VCR recording. |
| 11 | R-D-U-L | ▭⇦ | Start a trace tool. |
| 12 | L-D-U-R | ⇨▭ | Enter a calculation report screen. |
| 13 | R-L-D-U | ▭⇖ 33 | Go to the next stage in a defined exam protocol. This may change a combination of imaging parameters, stopwatch timers, image annotations, measurement tools and calculation package measurements. |
| 14 | L-R-D-U | 33↗▭ | Display the next entry in a series of pre-defined image annotation text strings. |

Explanation of pictographs:

| 12⟶▭ | = Transducer |
|---|---|
| 30⟶▽ | = Vector Image |
| 33⟶↝ | = Path of transducer motion |

*FIG. 6A*

METHOD AND APPARATUS FOR CONTROLLING ULTRASOUND IMAGING SYSTEMS HAVING POSITIONABLE TRANSDUCERS

TECHNICAL FIELD

This invention relates generally to methods and apparatus for controlling imaging systems and more particularly for controlling imaging systems having positionable transducers.

BACKGROUND

As is known in the art, one type of imaging system is an ultrasound imaging systems. A conventional ultrasound imaging system includes a positional transducer, typically a sonographer handheld transducer, coupled to a large processing and display workstation or operator interface. The frontal portion of the transducer includes an array of ultrasonic elements which transmit and receive ultrasonic energy for imaging a selected region of a patient. The received ultrasonic energy is converted to electric signals by the transducer and passed to the workstation. The workstation detects, filters and otherwise processes the information to generate a two- or three-dimensional representation of the scanned region.

The sonographer supplies the control signals for the workstation. Such control signals are typically supplied by the sonographer's free, or non-transducer carrying hand. Scanning situations in both the examination room and other locations often require the sonographer to be in awkward positions for simultaneously reaching the controls with the free hand and placing the frontal portion of the transducer in the proper position on the patient's body. One technique suggested to solve this problem is through voice activation; however, such technique may be prone to error and requires a speech recognition learning phase for each sonographer. Another technique suggested to provide the central signals to the workstation is through a sonographer actuated foot pedal; however such is not practical for all scanning situations.

SUMMARY

In accordance with the present invention, a method is provided for providing an operational command signals, sometimes herein referred to as control signals, to a workstation of an imaging system. The workstation is provided imaging data from a positionable transducer. One method includes converting at least one of a plurality of predetermined motion patterns imparted by an operator of the system to the transducer into the operational command signals.

With such method, the operator is provided with a way to control the workstation without taking a hand off of the transducer, or relying on voice control or foot actuated controls. The method reduces the number of times the operator must touch controls on the workstation.

Another method includes parting the transducer head into multiple regions (in one embodiment, less than four regions) and interpreting the reception of the signals from such regions into operational command signals.

A third method includes converting detections of predetermined echo signatures into operational command signals.

In one embodiment, the converting comprises detecting at least one of the predetermined motion patterns and converting such detected motion patterns into a corresponding one of the operational command signals.

In one embodiment, the detecting comprises comparing a sequence of images formed by the system.

In one embodiment, the method includes determining from the sequence of images whether the motion imparted to the transducer was either a repositioning of the transducer to produce a different image to be observed by the operator or a motion imparted to produce the corresponding one of the command signals to the workstation.

In one embodiment, such determining includes comparing types of motions imparted by the operation.

In one embodiment, such determining includes comparing imparted motion with a level threshold.

In one embodiment, such determining includes comparing imparted motion with a time duration threshold.

In one embodiment, a method is provided for providing control signals to a workstation of an imaging system, such workstation being provided imaging data from a positionable transducer. The method includes detecting patterns of motion of the transducer, and converting the patterns to the control signals.

In one embodiment, the detection is performed by detecting patterns of change in real time images provided by the system.

In one embodiment, timing of the motion is used to discriminate between motion intended to provide the control signals and motion normally occurring during scanning.

In one embodiment, patterns of direction of the transducer motion are used to discriminate between motion intended to provide the control signals and motion normally occurring during scanning.

In one embodiment, a combination of patterns of direction of the transducer motion and timing of the motion are used to discriminate between motion intended to provide the control signals and motion normally occurring during scanning.

In one embodiment, an imaging system is provided having a workstation and a positionable transducer for providing imaging data to the workstation. The workstation responds to the operational command signals. The workstation includes a memory for storing a table mapping detected motion of the transducer into the command signals.

In one embodiment, the workstation includes a processor programmed to detect at least one of a predetermined plurality of motion patterns and convert such detected one of the motion patterns into the operational command signals.

In one embodiment, the transducer has deposed within a housing thereof motion sensors.

In one embodiment, sensors disposed remote from the transducer sense motion of the transducer.

In one embodiment, an imaging system is provided having a workstation and a positionable transducer for providing imaging data to the workstation. The workstation responds to control signals. The workstation includes a processor for detecting patterns of motion of the transducer and converting the patterns to the control signals.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6A is a table showing the relationship between a repertoire of motions impartable by the operator to the transducer and the workstation control signals intended by the operator resulting from such motions;

Like reference symbols in the various drawings indicate like elements.

DETAILED DESCRIPTION

Figure 1:
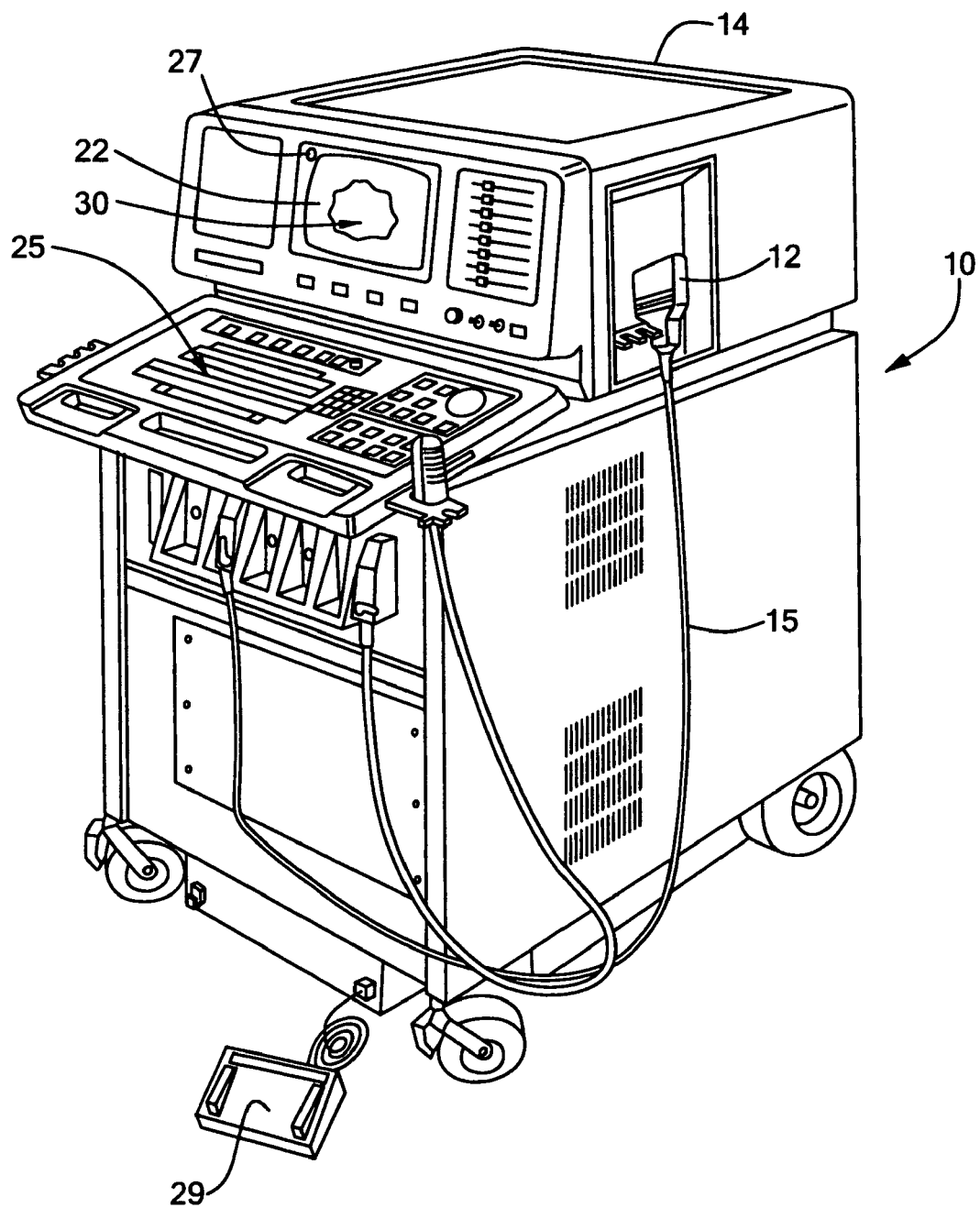
FIG. 1 is a sketch of an imaging system according to the invention.

FIG. 1 shows an imaging system 10, here an ultrasound imaging system for medical diagnostics. The system 10 includes a positionable, here handheld, image processing ultrasound device, here a transducer 12 shown in more detail in FIGS. 2A and 2B, and a multi-use display device, or operator interface, herein sometime collectively referred to as a workstation 14. The handheld transducer 12 obtains ultrasound data and formats the ultrasound data for transmission to the workstation 14, here via a cable 15. Controls to the workstation 14 are provided by detecting patterns of motion, to be described in more detail below, provided, or imparted, to the transducer 12 by an operator of the system 10, typically by a sonographer. Suffice it to say here that the pattern of motions may include: an up-down or down-up (i.e., axial) motion of the sonographer's transducer hand holding wrist (i.e., an up flick of the wrist followed by a down flick of the wrist or a sequence of down-up flicks of the wrist); a left-right or right-left (i.e., azimuthal) motion of the sonographer's transducer hand holding wrist (i.e., left-right flicks or right-left flicks of the wrist); for 2D arrays, a forward-and-backward (i.e., elevational) motion of the sonographer's transducer hand holding wrist; a inward-outward motion towards and away from the patient's body, or visa versa, or any combination thereof. The detection of these sonographer's imparted transducer motions may be performed by hardware and/or software to detect patterns of change in real time images. When motion is detected, the timing of the motion is used to discriminate between motion intended to initiate control changes and motion which occurs normally during scanning. In addition, patterns of direction are be used to discriminate between motion intended to initiate control changes and motion which occurs normally during scanning. The combination of timing and direction of transducer 12 motion changes are used to discriminate between transducer motion intended to initiate control changes and motion which occurs normally during scanning.

The transducer 12 includes a housing 16 (FIG. 2A) adapted to be easily handheld, such as for example, being less than 8 inches in any dimension and/or having an ergonomic shape for holding in a operator's hand. The housing 16 comprises plastic, rubber, metal, other materials now known or later developed, or combinations thereof. In one embodiment shown in FIG. 2A, the housing 16 is shaped for ergonomic use or holding by the operator (e.g., sonographer) by having a generally round or curved circumference handle serving as a grip for the sonographer's hand.

The handheld transducer 12 includes conventional ultrasound circuitry, not shown, within the housing 16. Thus, the ultrasound circuitry includes, in the frontal portion 20 thereof (FIGS. 2A and 2B) an array of ultrasonic elements 19 which transmit and receive ultrasonic energy for imaging a patient, not shown. It is noted that FIG. 2B is for a one-dimensional array transducer and FIG. 2D is for a 2D array transducer. Here, the transducer's transmit and receive elements 19 in the frontal portion 20 are arranged in an elongated array along a the longer axis, here the Y axis of the rectangular shaped patient interfacing surface, i.e., the frontal portion 20, of the housing 16. The elements 20 in the frontal portion 20 are, as shown in FIG. 3 fed to a display 22 of the workstation 14 (FIG. 1) serially through: a beamforming network 24, an echo processor 26, a scan converter 28, and an image processor 31 in a conventional manner. The beamforming network 24, echo processor 26, scan converter 28, image processor 31 and display 22 are controlled by a central processing unit (CPU) 32 coupled to a random access memory RAM 37. The CPU 32 operates in accordance with program instructions stored in a ROM 34, or in RAM 37, or in flash memory not shown, or on a hard drive device, not shown. A memory 36, here an erasable, or other type of programmable semiconductor memory, here a read only memory (ROM) is provided for storing a computer, here microprocessor, executable program, for operating the CPU 32 as described herein. Further, the RAM 37 stores, after being read from the hard drive, not shown, a table (TABLE I) mapping detected motion imparted by the operator of the transducer 12 into command, or control, signals for the workstation 14 (FIG. 1). Further it should be noted that the user might alter the mapping provided by the table using setup screen touch commands.

Thus, the ultrasound processor 21 (FIG. 3) scan converts data associated with the radial scan pattern to generate ultrasound image data in a video format (e.g. Cartesian coordinate format). In one embodiment, a single radial scan format with possible changes in depth limits the number of operations for scan converting. Multiple scan formats and associated scan conversions may be used. Video filtering or processing may also be provided. Thus, as noted briefly above, the processor 21 (FIG. 3) includes the array of transmitting/receiving elements 18, here an array of piezoelectric crystals that deliver ultrasonic energy into a patient and receive ultrasonic echoes from the patient. Electrical signals representative of the echoes produced by the transducer 12 are delivered to the beamforming network 24 where they are selectively combined to produce an indication of the echo intensity along a particular direction or beam in the patient. The data produced by the beamforming network 24 is fed to the echo processor 26 that calculates echo intensity at each position along a beam and may calculate a Doppler shift of the echoes received along a particular beam. Data from the echo processor 28 is fed to a scan converter 28 that converts the data into a form that can be readily displayed on a video monitor 22.

The data produced by the scan converter 28 is stored in the RAM 37 where an additional processing, such as adding color, may be performed prior to displaying the images on a video monitor. Controlling the operation of the above-referenced parts are one or more central processing units, here collectively indicated by the CPU 32. The central processing units also receive commands from the sonographer. As noted above, controls to the workstation 14 are provided by detecting patterns of motion, to be described in more detail below, provided to the transducer 12 by the sonographer. Thus, the CPU 32 together with the image data stored in RAM 37 and the TABLE I stored in memory 36, processes the motion detection signals imparted by the sonographer to provide these workstation control signals. Recognition of the motion inputted command by the processor 21 results in the CPU 32 sending a signal to a light and/or buzzer 27 mounted on the workstation 14, or changing some on-screen indicator. Activation of the light and/or buzzer or on screen indicator 27 provides a visual and/or audible indication to the sonographer that the command has been completed.

It should be understood that the commands or control signals provided to the workstation 14 by detecting patterns of motion provided to the transducer 12 by the sonographer may be supplemented by other tactile commands entered manually by the sonographer to the workstation keyboard 25 (FIG. 1) or by a foot pedal 29 (FIG. 1). In either case, these controls allow the sonographer to adjust the operation of the ultrasound machine workstation 14. In addition, some command or control signals may be sent after some configurable delay after the pattern of motion is detected. This will allow controls which require a stable image, such as image capture, to be included in the command table.

Figure 2A:
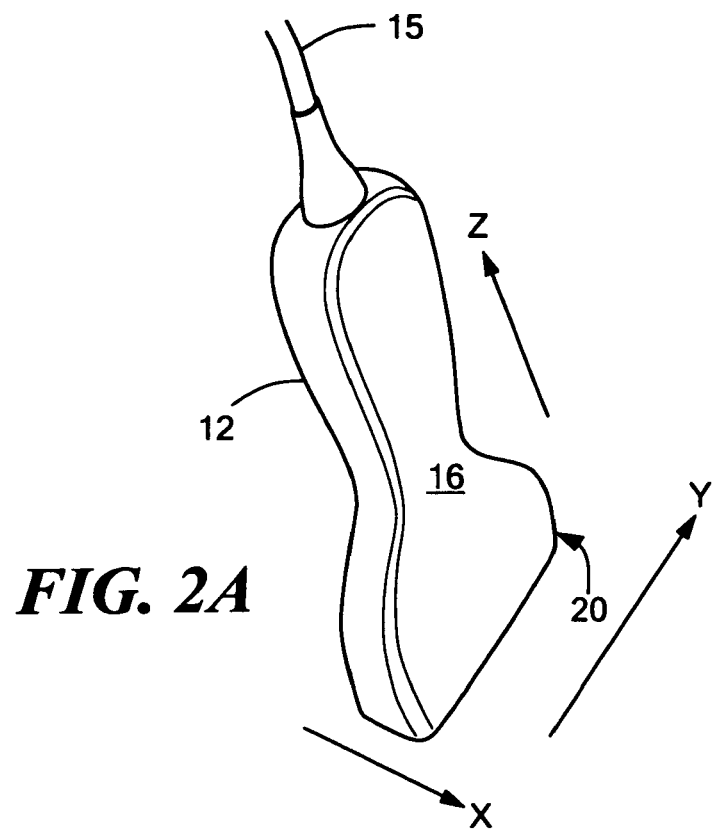
FIG. 2A is an isometric sketch of a transducer used in the system of FIG. 1.
Figure 2B:
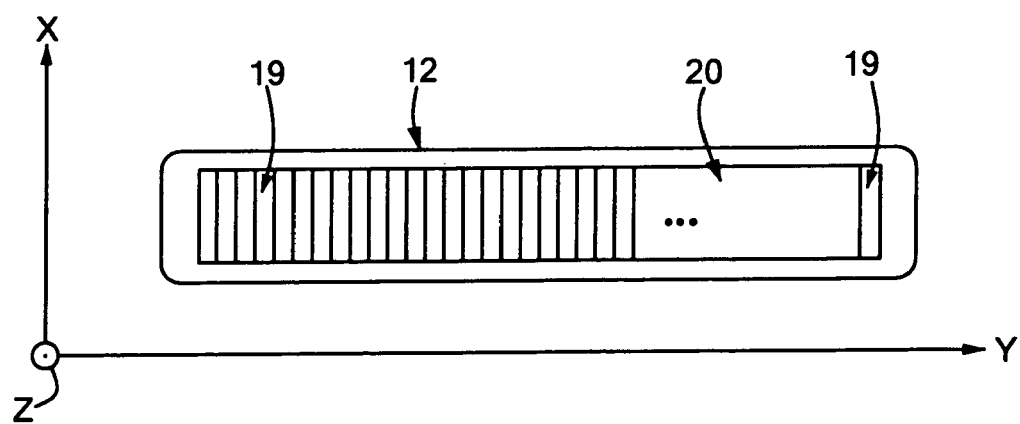
FIG. 2B is a front elevation view of the frontal portion of the transducer of FIG. 2A.
Figure 3:
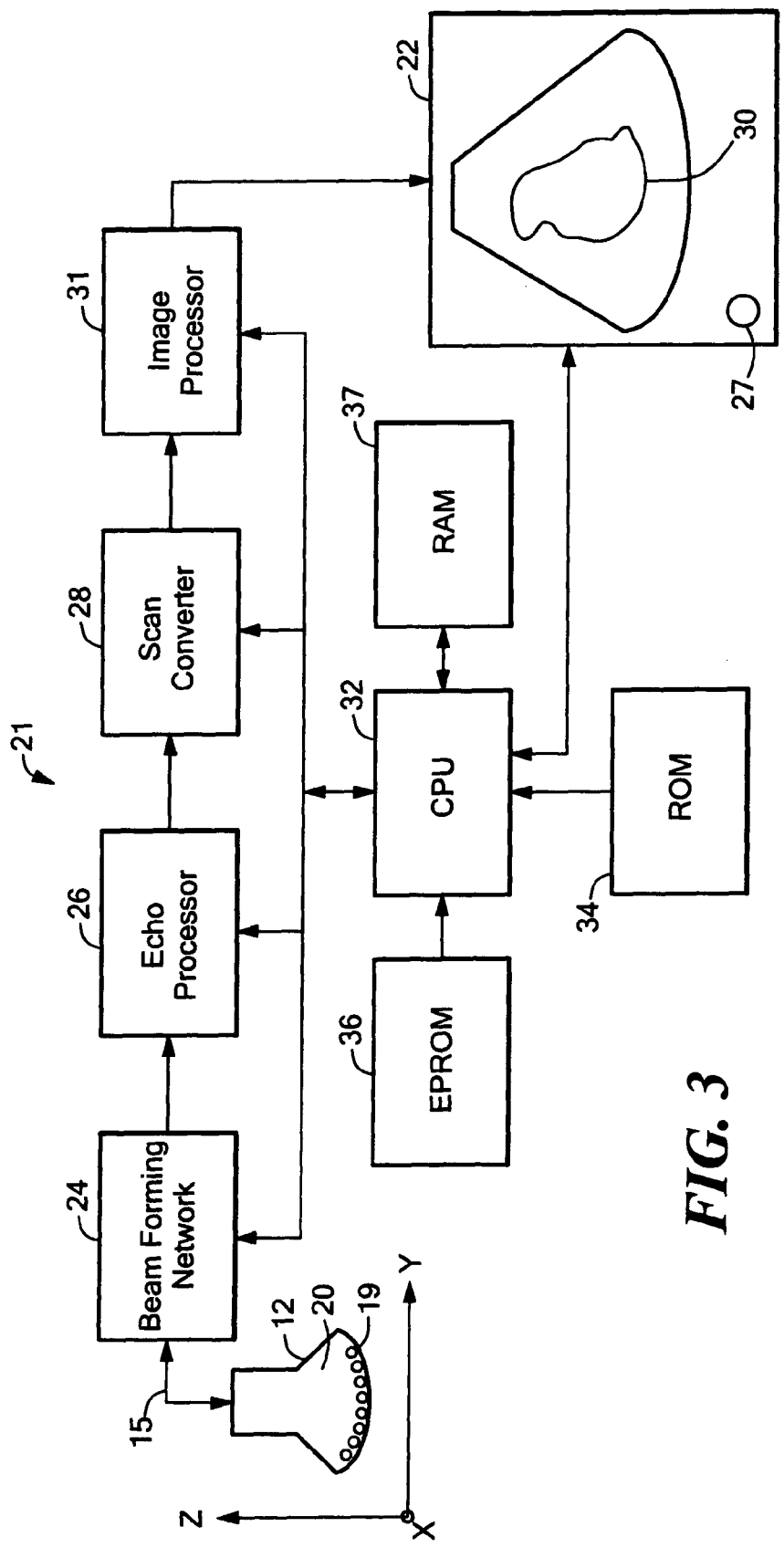
FIG. 3 is a block diagram of a processor used to process imaging data from the transducer of FIGS. 2A and 2B to generate an image for an operator of a workstation used in the system of FIG. 1 and to process such data to generate control signal for operation of the workstation.

The transducer 12, as noted above, includes transmit and receive elements 19 (FIGS. 2A and 2B). These elements 19 are arranged to provide an array of elements for transducing between acoustical and electrical energies, such as a one-dimensional, 1.5D, two-dimensional or single element transducer. Any of a phased array, linear array, curved array or other arrays may be used. An acoustic window, not shown, is disposed in the frontal portion 20 on the housing 16 adjacent to the transducer 12.

As noted above, the transducer 12 is electrically coupled to the workstation 14 (FIG. 1) by a cable 20. It should be noted that the transducer 12 might be wireless coupled to the workstation 14 as described in U.S. Pat. No. 6,780,154 issued Aug. 24, 2004, inventors Hunt et al., assigned to the same assignee as the present invention, the entire subject matter thereof being incorporated herein by reference.

Referring now again to FIGS. 2A and 2B, it is noted that the housing 16 of the transducer 12, and more particularly the frontal portion 20 thereof having the array, here a one or two-dimensional array, of transmitting and receiving elements, not shown, is rectangular shaped, having its longer dimension along a, here Y, or azimuthal axis, and its shorter dimension along, here, the X, or elevation, axis, as indicated. An axial Z axis is thus along the length of the housing (i.e., an axis perpendicular to both the X and Y axes to provide a conventional Cartesian coordinate system for the transducer 12.

Figure 4A:
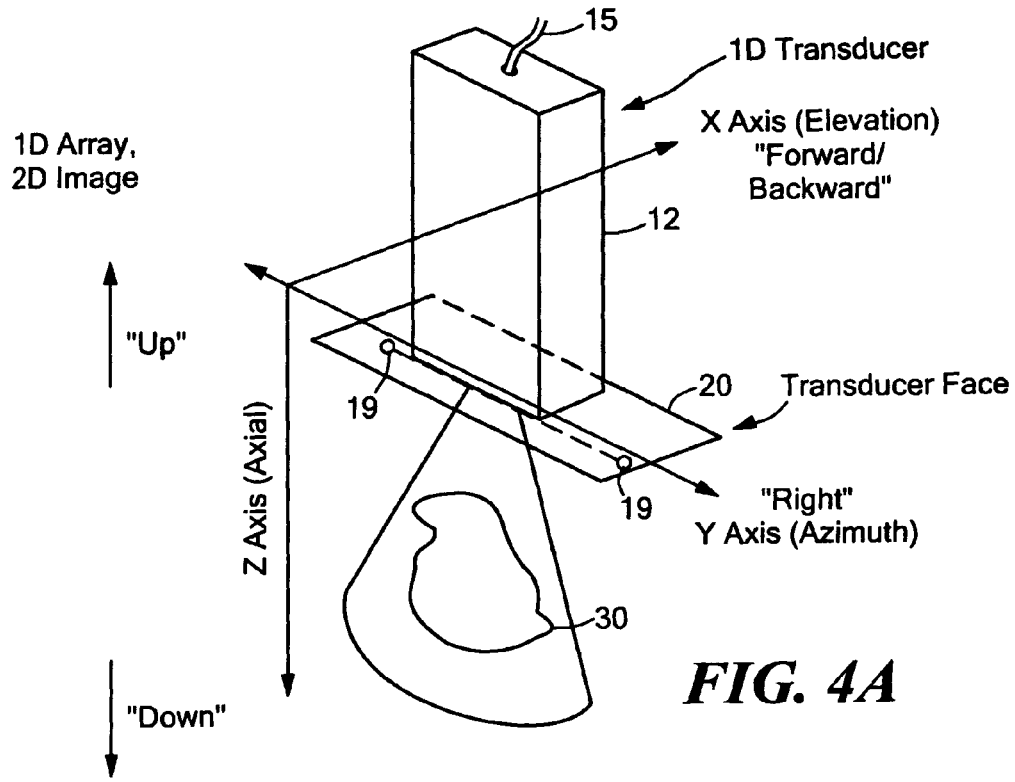
FIG. 4A is a diagram showing a coordinate system for a one-dimensional array transducer used in the system of FIG. 1, such coordinate system indicating and defining operator motion of the transducer.

FIG. 4A shows the region of a scan of an image 30, here a sonogram, produced by placing the transducer 12 at one fixed position on the patient's body, not shown. It is first noted that the transducer 12 shown in FIG. 4A has a one-dimensional array of the transmit/receive elements 19. It is next noted that the image 30 is the Y-Z plane of the transducer's coordinate system described above in connection with FIGS. 2A and 2B. Here, for this one dimensional array transducer we define the following directions of motion impartable by the sonographer to the transducer 12:
(1) a upward (U) motion is a motion along the −Z axis;
(2) a downward (D) motion is a motion along the +Z axis;
(3) a leftward (L) motion is a motion along the −Y axis; and
(4) a rightward (R) motion is a motion along the +Y axis.

Figure 4B:
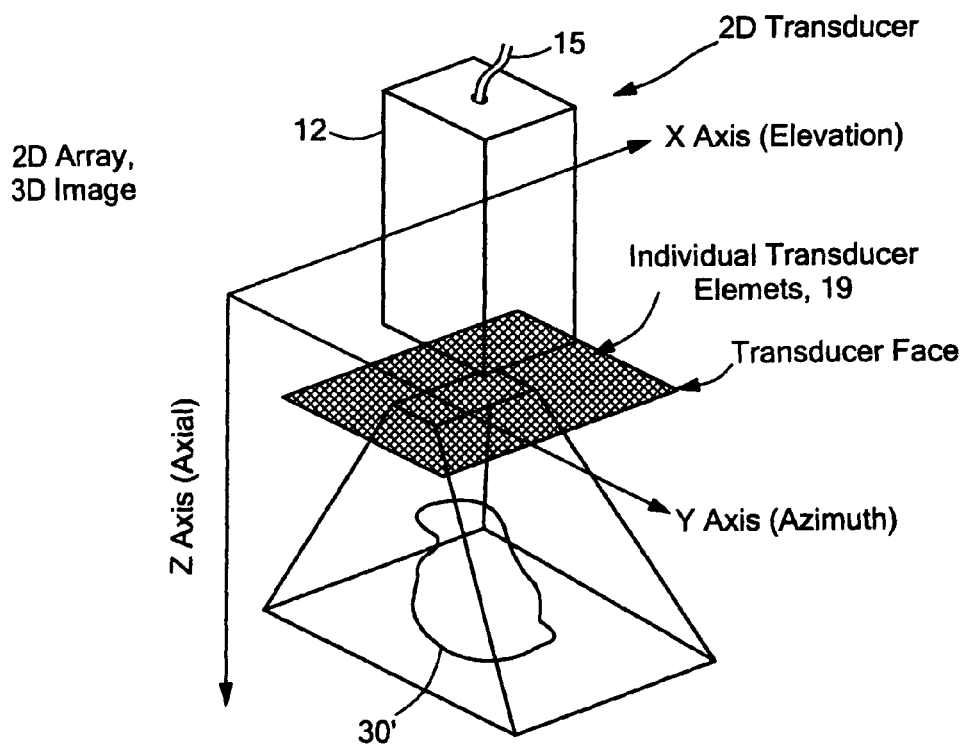
FIG. 4B is a diagram showing a coordinate system for a two-dimensional array transducer used in the system of FIG. 1, such coordinate system indicating and defining operator motion of the transducer.

FIG. 4B shows the region of a scan of an image 30 produced by a transducer 12 having a two dimensional array of elements 19. It is noted that image 30' produced by this two dimensional array transducer is a three-dimensional image 30'. Here, for this two-dimensional array transducer, we define the following directions of motion impartable by the sonographer to the transducer 12:
(1) a forward (F) motion is a motion along the +X axis;
(2) a backward (B) motion is a motion along the −X axis;
(3) a upward (U) motion is a motion along the −Z axis;
(4) a downward (D) motion is a motion along the +Z axis;
(5) a leftward (L) motion is a motion along the −Y axis; and
(6) a rightward (R) motion is a motion along the +Y axis.

The ultrasound system 10 (FIG. 1) is capable of displaying the image 30 in either orientation, (also U/D inverted) it is simply an operator preference. A small symbol, not shown, is displayed on the screen 22 which corresponds to a physical notch, not shown, on the transducer 12 housing so the operator (and anyone viewing the images later) can tell which way the image is oriented. In FIGS. 4A and 4B the surface the patient, not shown, is in the X-Y plane, and the Z axis is "into" the patient's body.

It should be understood that, as is well known, the term "Linear array" refers to a one-dimensional (1D) array used to produce a "Linear" image, while a "Sector array" or "Vector array" refers to a 1D array used to produce a "Sector" image. The physical geometry of the transducers is similar, but vector arrays tend to be smaller. The shape of the image is determined by the way the systems controls the electrical timing of the transmit and receive signals. A third image format is the "Curved Linear" image, produced by a linear transducer with a convex curve along the azimuthal dimension of the transducer surface.

Figure 5A:
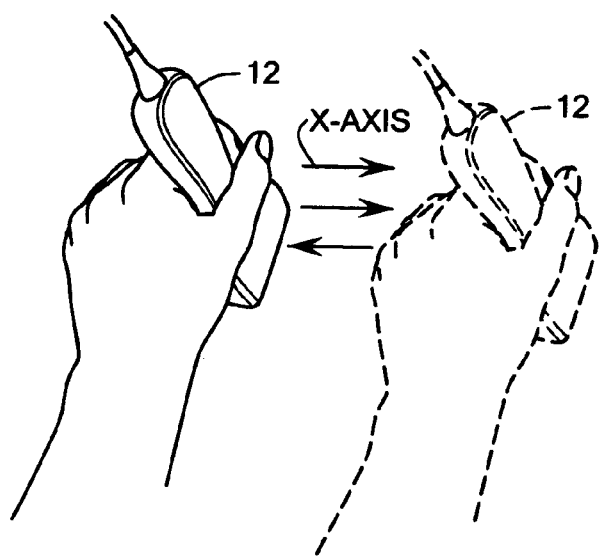
FIGS. 5A, 5B and 5C show various patterns of motion which may be imparted to the transducer by the operator and then image data which is processed by the processor of FIG. 3 to generate the control signally for the workstation of the system of FIG. 1.
Figure 5B:
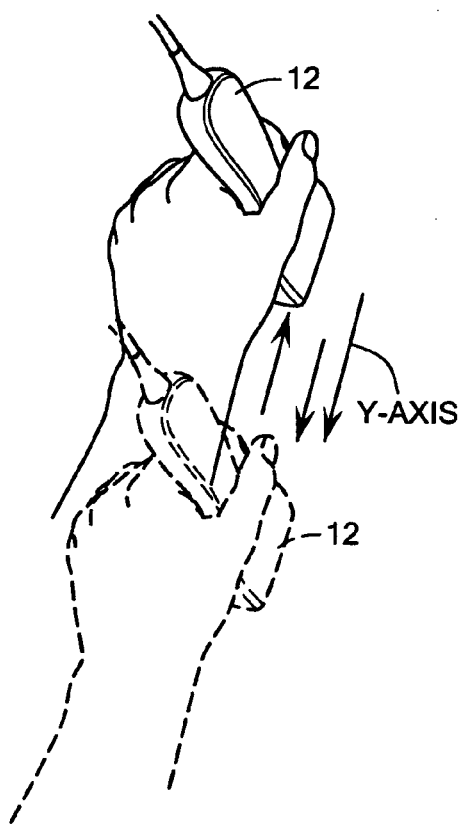
Figure 5C:
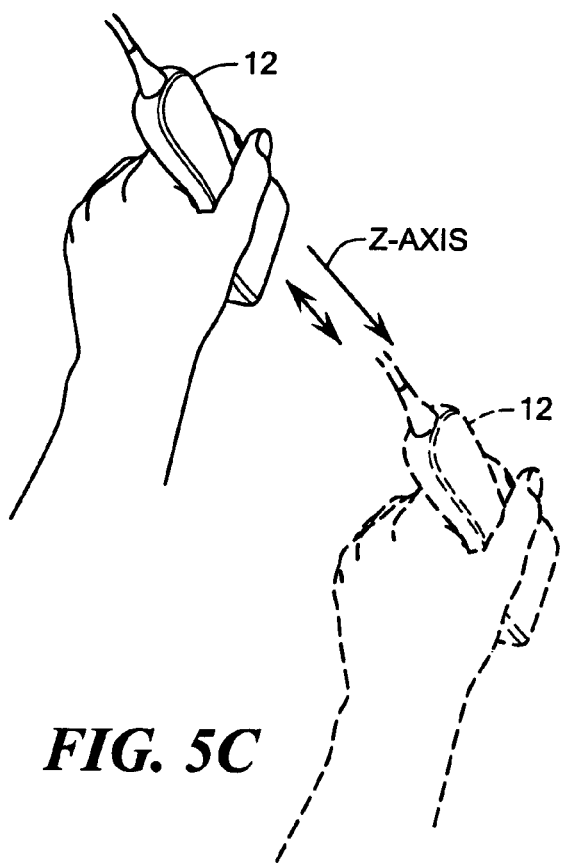

FIG. 5A shows of a motion of the transducer 12 by the sonographer along the X-axis (i.e., a forward/backward motion); FIG. 5B shows of a motion of the transducer 12 by the sonographer along the Y-axis (i.e., a right (R)/left (L) motion; and, FIG. 5C shows of a motion of the transducer 12 by the sonographer along the Z-axis (i.e., an up (U)/down (D) motion.

As noted above, the processor 21 (FIG. 3) detects patterns of these X, Y and/or Z sonographer imparted motions to provide controls to the workstation 14. The invention consists of software and/or hardware to detect patterns of transducer motion, and hardware and/or software to map those patterns to the activation of system controls. The detection of these sonographer's imparted transducer motions may be performed by hardware and/or software to detect patterns of change in real time images. When motion is detected, the timing of the motion are be used to discriminate between motion intended to initiate control changes and motion which occurs normally during scanning. As noted above, patterns of direction are used to discriminate between motion intended to initiate control changes and motion which occurs normally during scanning. The combination of timing and direction of transducer 12 motion changes are used to discriminate between transducer motion intended to initiate control changes and motion which occurs normally during scanning.

Figure 6B:
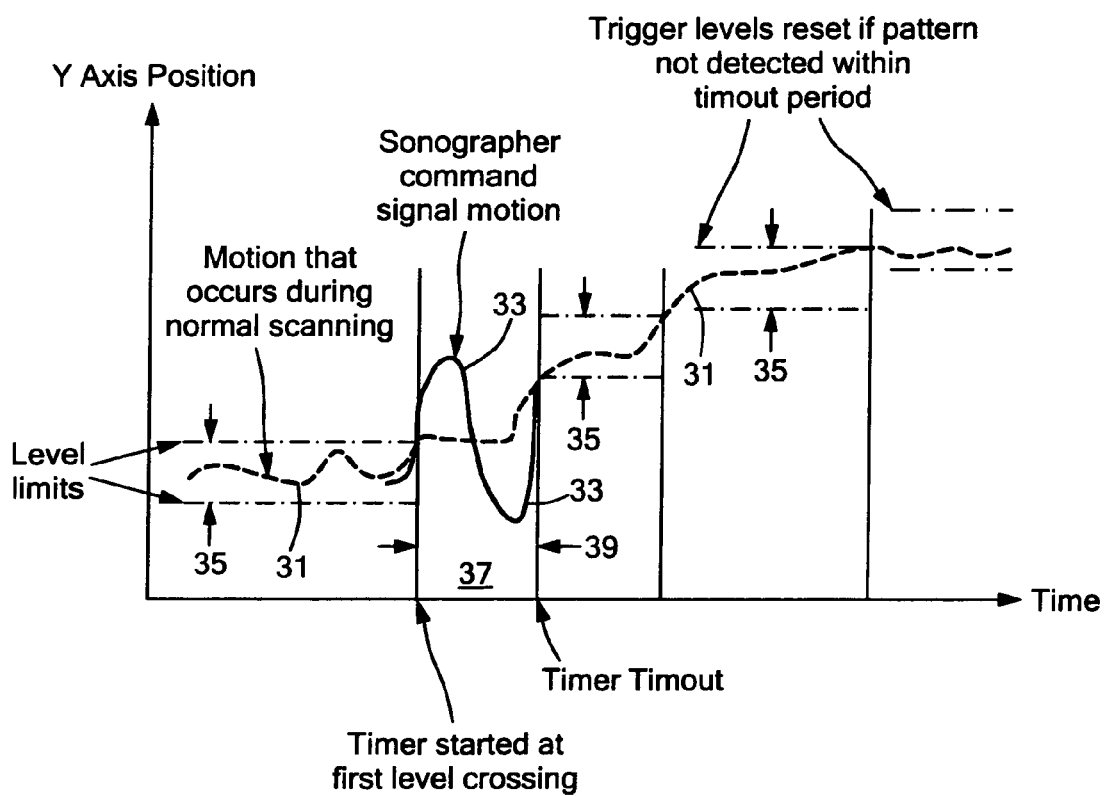
FIG. 6B shows a comparison between normal transducer motion occurring during scanning and motion used to initiate a command signal to the workstation of FIG. 1.

More particularly, the Table I below and stored in memory 36 (FIG. 3) provides an exemplary repertoire of motions imparted to the transducer by the sonographer and which are interpreted by data stored in a Table II below of the memory 36, e.g., an EPROM, of the processor as command, or control signals for the workstation. Thus, the memory stores a table (TABLE I, below) mapping, in this example 14 detectable motions of the transducer 12 each one of the 14 motions (i.e., identified by the designations "ID1" through "ID14") corresponding to one of 14 command signals for the workstation 14, as indicated in FIG. 6A. It is noted that each one of the exemplary patterns 33 (FIG. 6A) in TABLE I is different from merely changing the position of the transducer 12 to obtain a different scan view. For example, a sequence of a left flick of the wrist followed by a right flick of the wrist is not the type of motion used to merely change the scan view. Further, it is noted that each pattern includes a sequence of at least two flicks of the wrist (each pair of flick typically occurring in a second of time or less). Still further, a single flick of the wrist, as shown by the curve 33 in FIG. 6B may be used assuming it is fast compared with the motion typically, or normally, used to change transducer image position shown by the curve 31 in FIG. 6A.

TABLE I

| ID | Name | Description |
|---|---|---|
| 1 | R-L | The transducer is moved to the right, then back to the original position |
| 2 | L-R | Transducer moved to the left, then back to the original position |
| 3 | R-L-R-L | Transducer moved to the right, back to the original position, then back to the right and finally back to the original position. |
| 4 | L-R-L-R | Transducer moved to the left, back to the original position, then back to the left, and finally back to the original position. |
| 5 | R-L-L-R | Transducer moved to the right, to the left past the original position, then back right to the original position. |
| 6 | L-R-R-L | Transducer moved to the left, to ther right past the original position, then back to the original position. |
| 7 | D-U | Transducer moved down, then back up. |
| 8 | U-D | Transducer moved up, then back down. |
| 9 | D-U-D-U | Transducer moved down, then back up, then the motion is repeated. |
| 10 | U-D-U-D | Transducer moved up, then back down, then the motion is repeated. |
| 11 | R-D-U-L | Transducer moved to the right, then down, then up, then back to the original position |
| 12 | L-D-U-R | Transducer moved to the left, then down, then up, then back right to the original position |
| 13 | R-L-D-U | Transducer moved to the right, left, down, and back to the original position |
| 14 | L-R-D-U | Transducer moved to the left, right, down, and back up to the original position. |

TABLE II

| ID | Name | User interface action |
|---|---|---|
| 1 | R-L | Capture the image and store it in a patient database.. |
| 2 | L-R | Start capturing image data to a movie clip. |
| 3 | R-L-R-L | Mouse Right click, bring up a menu. |
| 4 | L-R-L-R | Mouse double click, select a user interface object, such as a menu item. |
| 5 | R-L-L-R | Invoke an on-screen cursor. |
| 6 | L-R-R-L | Select the next measurement in a series of measurements. |
| 7 | D-U | Mouse left click |
| 8 | U-D | Start automatic image gain adjustment |
| 9 | D-U-D-U | Start VCR recording |
| 10 | U-D-U-D | Stop VCR recording |
| 11 | R-D-U-L | Start a trace tool |
| 12 | L-D-U-R | Enter a calculation report screen |
| 13 | R-L-D-U | Go to the next stage in a defined exam protocol. This may change a combination of imaging parameters, stopwatch timers, image annotations, measurement tools and calculation package measurements. |
| 14 | L-R-D-U | Display the next entry in a series of pre-defined image annotation text strings. Enter cine review playback Start voice activation listening Start voice annotation recording Stop voice annotation recording |

Figure 2C:
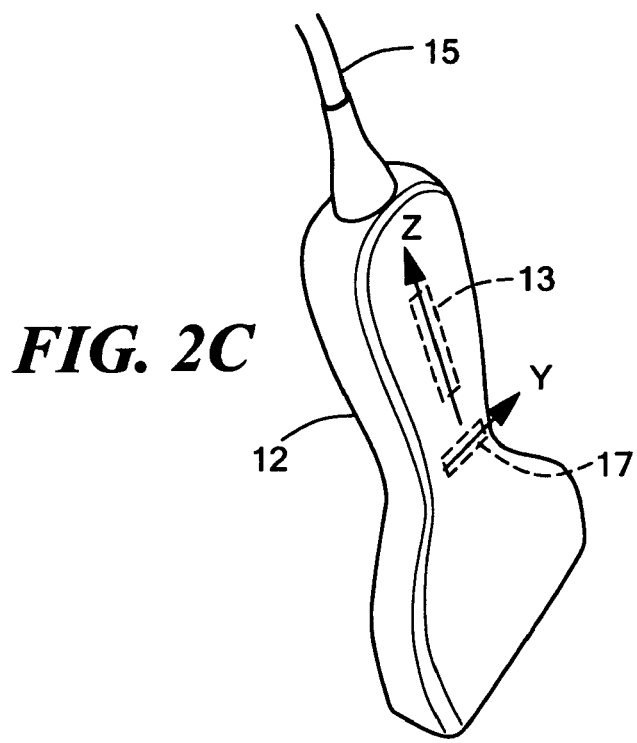
FIG. 2C is an isometric sketch of a transducer adapted for use in the system of FIG. 1 according to one embodiment of the invention.
Figure 2D:
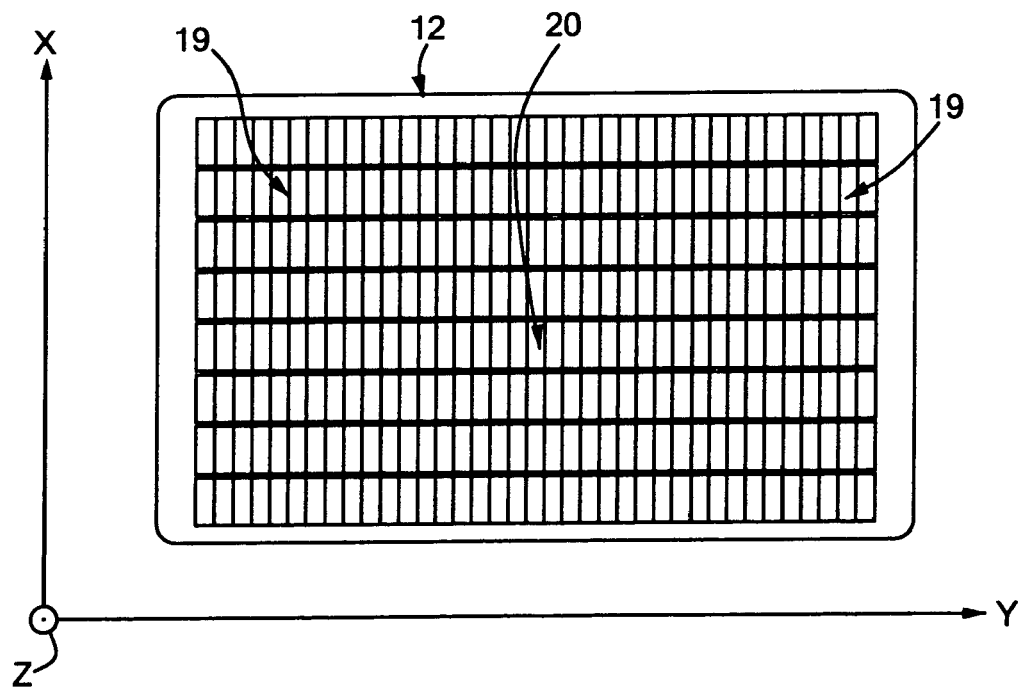
FIG. 2D is a front elevation view of the frontal portion of a 2D array transducer.
Figure 9:
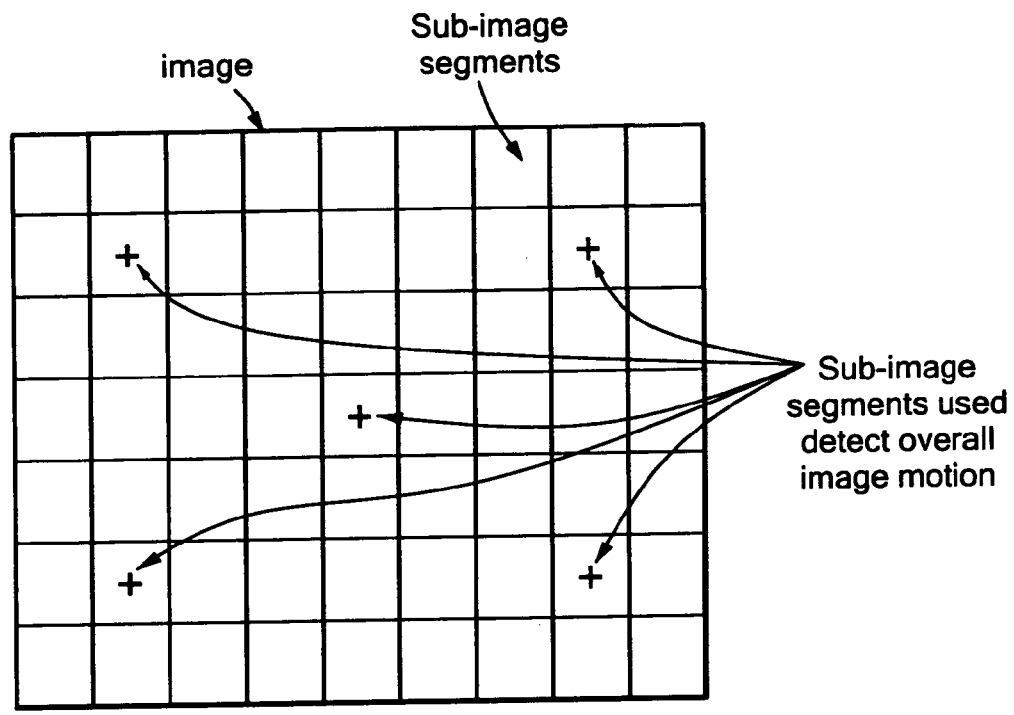
FIG. 9 is a diagram showing an image obtained by the processor of FIG. 3 divided into sub-image segments by the processor and used to detect overall image motion.

The motion detection (i.e., U, D, L and R) may be performed in any one of a variety of ways. For example, the detection of transducer motion may be done using decimated image data; using Doppler Tissue Imaging, (FIG. 9) in which dedicated hardware or software will average the computed Doppler velocity and/or Doppler energy signals from a sample set of echo information at a predetermined set of image locations 91; or in a like manner but with the predetermined set of image locations confined to the near-field of the image, using a pair of micromachined accelerometers 13, 17 (FIG. 2C) such as model series ADXL manufactured by Analog Devices, Norwood, Mass., one disposed within the housing 16 of the transducer 12 along the Y axis, and other disposed along for example, either along the X axis or the Z axis, as shown in FIG. 2C, a rate gyro for sensing twisting or rolling motion of the wrist, such a model series ADXRS manufactured by Analog Devices, Norwood, Mass. or other motion-sensing device disposed within the housing 16 of the transducer 12; or by a video monitoring camera. Signals from the motion-sensing devices mentioned above disposed within the housing 16 are coupled from the transducer 12 to the workstation 14 through cable 15, or wireless. Another technique may include mounting light emitting diodes to the transducer body and having light detecting sensors fixed to the workstation or examination room remote from the transducer. One such system is manufactured by Northern Digital (NDI), International Headquarters 103 Randall Drive Waterloo, Ontario Canada N2V 1C5.

One technique used to detect transducer motion is described in U.S. Pat. No. 6,162,174 entitled "Method for compensating for object motion in ultrasound images", issued Dec. 19, 2000, inventor Friemel, assigned to the same assignee as the present invention, the entire subject matter thereof being incorporated herein by reference. While there transducer motion is detected to remove image flicker, the method included determining transducer motion. As noted above, when motion is detected, the timing of the motion are be used to discriminate between motion intended to initiate control changes and motion which occurs normally during scanning. In addition, patterns of direction are be used to discriminate between motion intended to initiate control changes and motion which occurs normally during scanning.

The combination of timing and direction of transducer 12 motion changes are used to discriminate between transducer motion intended to initiate control changes and motion which occurs normally during scanning.

Figure 7:
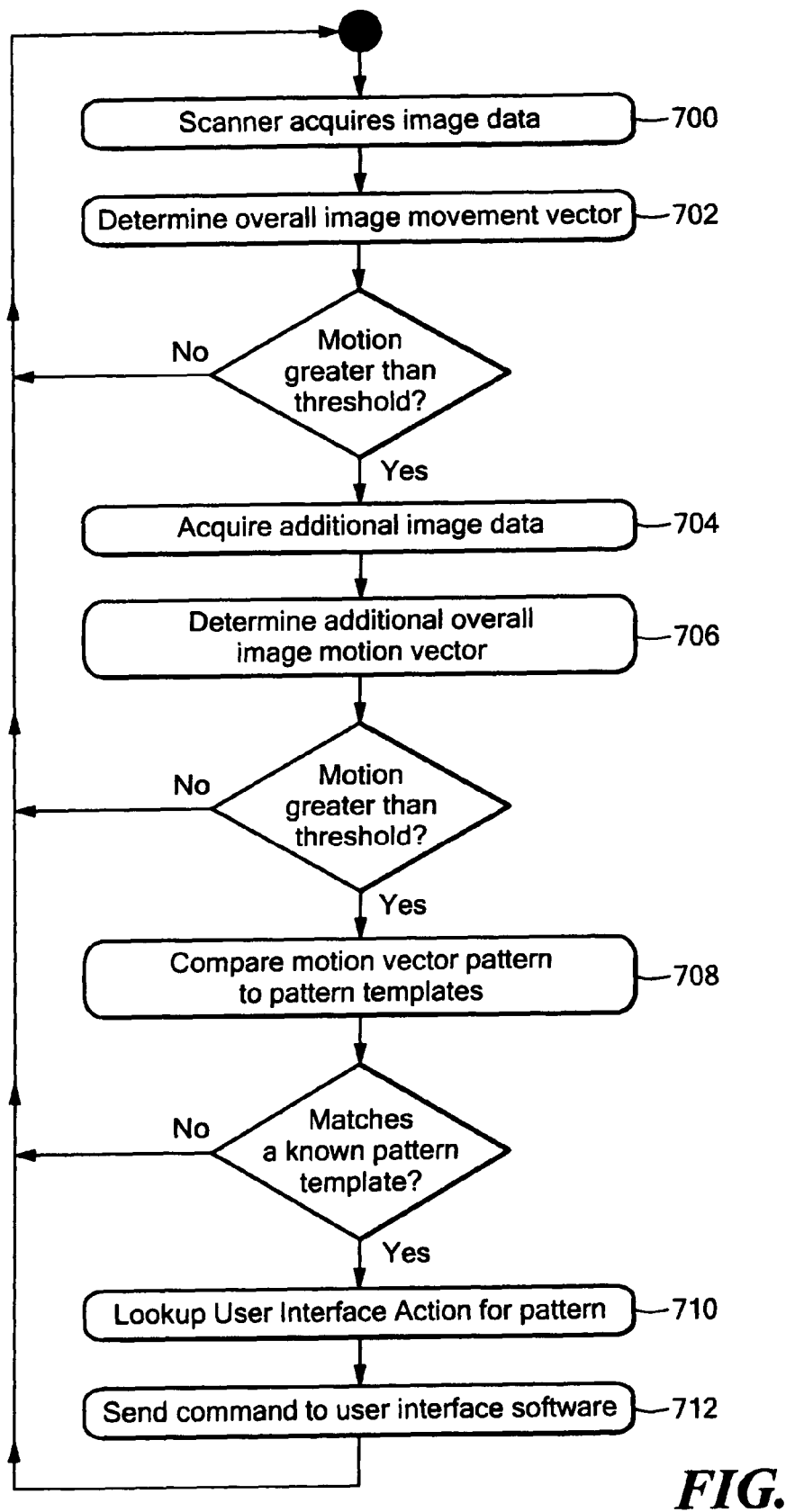
FIG. 7 is a flow diagram of a process used by the processor of FIG. 3 in generating the workstation control signals from images generated by the transducer.

Referring now to FIG. 7, a flow diagram of one method used herein to generate workstation commands from sonographer imparted motions to the transducer is shown.

The scanner (i.e., scanning system) acquires image data (Step 700). The processor 21 (FIG. 3) determines the overall image motion vector (Step 702). If the determined overall image movement vector is greater than a predetermined threshold (i.e., the motion is consistent with the flick of the sonographer's wrist or a rapid up-down motion of the transducer as distinguished from a motion consistent with the sonographer merely changing the position of the transducer to obtain a different view of the region being observed of the patient) the processor 21 acquires additional image data and stores such data in RAM 34 (Step 704). It is noted that, in general, the magnitude threshold filters out normal, small movements of the sonographer's hand, while the pattern matching filters out normal movement to obtain a different field of view. Further, one type of filter which may be useful would be a high pass filter or differentiator to produce an output signal related to the rate of change of the motion, i.e. the slope of the curve shown in FIG. 6B. Thus, referring to FIG. 6B, whenever the magnitude of the motion, i.e., the Y axis in this example, exceed a predetermined threshold, or window 35, as in time region 37, a timer, not shown, in the CPU 32 (FIG. 3) is activated. i.e., indicated as "Timer started at first level crossing". If a second motion exceeding the motion limits is detected before the time duration exceeds, a predetermined time duration window 37, a command signal is recognized by the CPU 32. If a single motion exceeds the motion threshold limits, but is not followed by a second motion prior to the timer expiration, the position limits will be reset to the current position.

Next, in Step 706, the processor 21 determines additional overall image motion. This may be achieved by the means described in one of the means (e.g., low pass filter) described above. If the determined overall image movement vector is greater than a predetermined threshold (i.e., the motion is consistent with the sonographer's intention to generate a control signal for the workstation 14), a motion vector pattern is compared to pattern templates at Step 708.

Now the process has determined a sequence of two motions. This pattern is now fed to the memory-36 storing TABLE I and the information is used by TABLE II also stored in memory 36 (Step 710) to provide the corresponding control signals to the workstation 14 (Step 712). Also, the light and/or buzzer 27 is activated to provide a visual and/or audible indication to the sonographer that the command has been completed.

Figure 8:
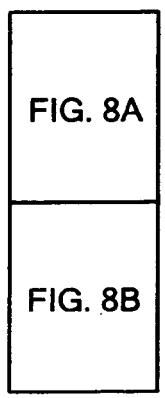
FIGS. 8, 8A and 8B are flow diagrams in more detail of the process of FIG. 7 used by the processor of FIG. 3 in generating the workstation control signals from images generated by the transducer.
Figure 8B:
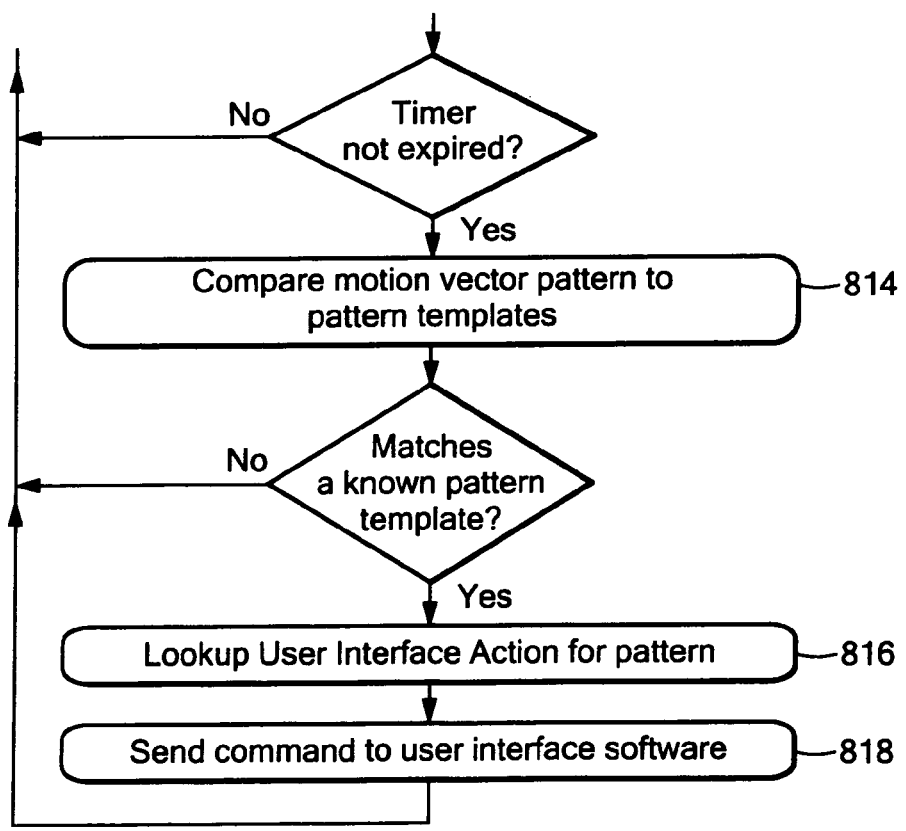
Figure 8A:
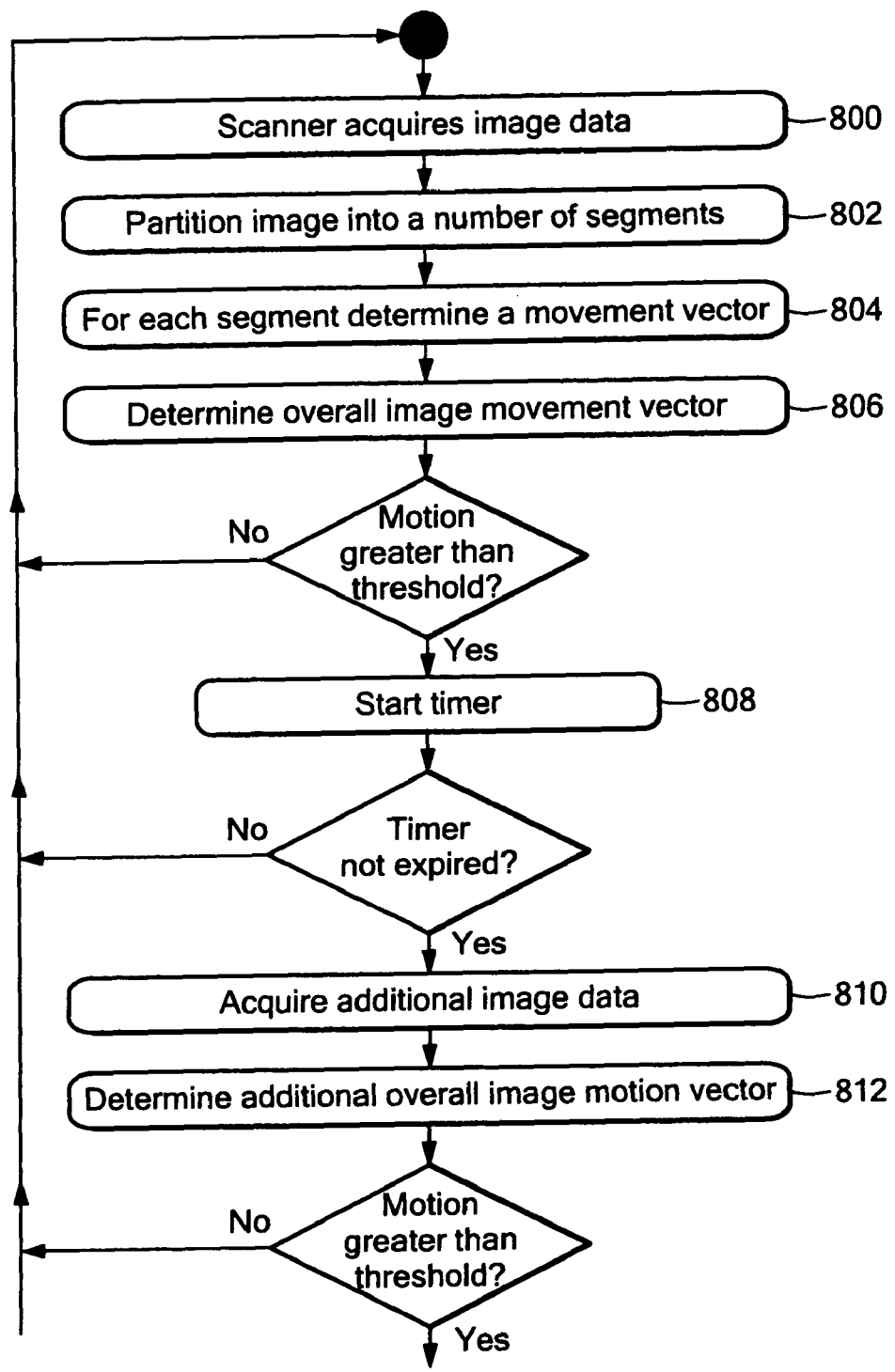
Figure 10:
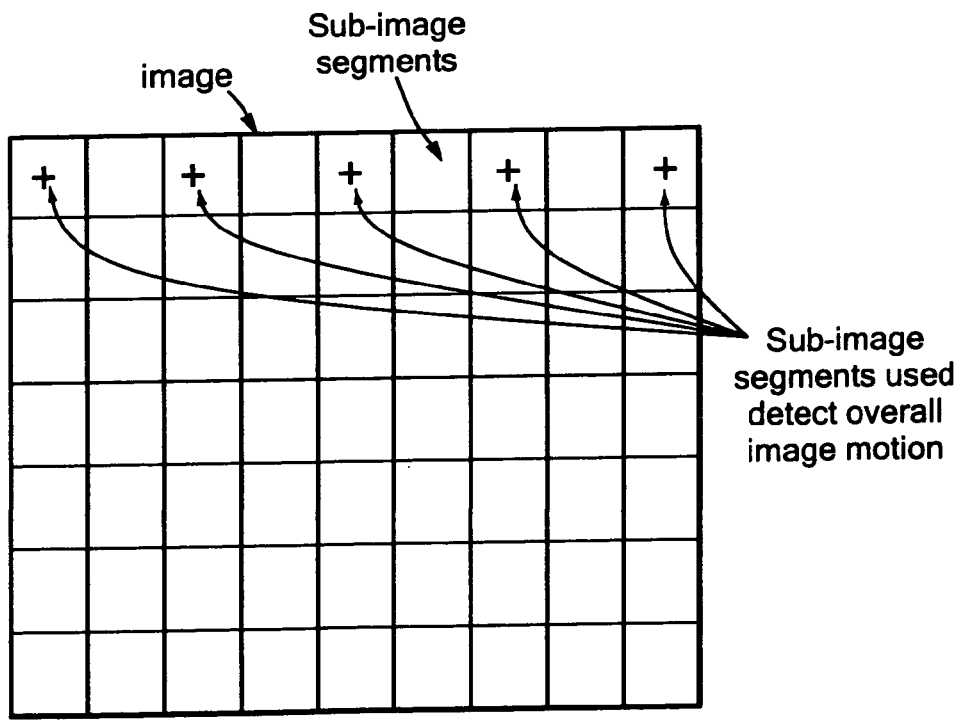
FIG. 10 is a diagram showing an image obtained by the processor of FIG. 3 divided into sub-image segments by the processor with near-field segments used to detect overall image motion.

A more detailed flow diagram is shown in FIG. 8, which further includes FIGS. 8A and 8B. Again the scanner acquires image data to generate an image (Step 800). The processor 21 (FIG. 3) partitions the generated image 30, 30' into a plurality of segments, not shown, Step 802. For each segment the processor 21 determines a movement vector, not shown, Step 804. From the plurality of vectors, the processor 21 determines the overall image motion vector, not shown, Step 806. More details of Steps 802 through 806 are provided in the above-identified in U.S. Pat. No. 6,162,174. Another technique to detect motion is to select a number of strategic image segments, measure the Doppler velocity or energy of each, and add up the velocity vectors. If there is a moving structure in the body in one of the segments, it will be averaged out by the other vectors and produce a small vector, while if the transducer is moving, the sum of the vectors will be relatively large. One possible placement of the image segments used to detect transducer motion is a selection of image segments in the near-field of the image, as shown in FIG. 10. Such a placement minimizes the effect of normal motion of organs within the body causing false transducer motion detection.

If the determined overall image movement vector is greater than a predetermined threshold (i.e., the motion is consistent with the flick of the sonographer's wrist or a rapid up-down motion of the transducer as distinguished from a motion consistent with the sonographer merely changing the position of the transducer to obtain a different view of the region being observed of the patient), the processor 21 acquires additional image data and the processor starts a timer, not shown, in the CPU 32 (FIG. 3), Step 808.

Again the scanner acquires image data to generate an image 30, 30', Step 810. The processor 21 partitions the generated image into a plurality of segments, not shown, for each segment the processor determines a movement vector, and from the plurality of vectors, the processor determines the overall image motion vector, Step 812.

If the determined overall image movement vector is greater than a predetermined threshold (i.e., the motion is consistent with the flick of the sonographer's wrist or a rapid up-down motion of the transducer as distinguished from a motion consistent with the sonographer merely changing the position of the transducer to obtain a different view of the region being observed of the patient), and the timer has not expired, i.e., the overall motion has not exceeded a predetermined time, (i.e., the processor 21 has determined a sequence of two motions, the processor 21 compares the motion vector to the vectors stored in TABLE I and the information from TABLE I is used by TABLE II, Step 816 to provide the corresponding control to the workstation Step 818. Also, the light and/or buzzer 27 is activated to provide a visual and/or audible indication to the sonographer that the command has been completed.

It should be noted that the method described above compares types of motions imparted by the operation. Further, the method described above compares imparted motion with a level threshold. Still further, the method described above compares imparted motion with a time duration threshold. Thus, the method described above comprises detecting patterns of motion of the transducer, and converting the patterns to the control signals. The detection is performed by detecting patterns of change in real time images and/or real time Doppler frequency shift information provided by the system. Further, timing of the motion is used to discriminate between motion intended to provide the control signals and motion normally occurring during scanning. It should be understood that patterns of direction of the transducer motion may used to discriminate between motion intended to provide the control signals and motion normally occurring during scanning. Likewise, timing of the motion is used to discriminate between motion intended to provide the control signals and motion normally occurring during scanning, or a combination of timing and direction may be used for such discrimination.

A number of embodiments of the invention have been described. Nevertheless, it will be understood that various modifications may be made without departing from the spirit and scope of the invention. For example, other commands may be used such as, for example: The operator may press the transducer slightly down and back up to the original position. The detection of this may be mapped to the action of moving to the next step in a protocol driven exam; the operator may move the transducer slightly left and back right to the original position. This may be mapped to pressing the image store key; the operator may move the transducer slightly left and back right to the original position. This may be mapped to increasing the image depth. The operator may remove the transducer from the patient and re-apply it causing the current calculation package to advance to the next measurement. The operator may move the transducer back and forth twice in a "double-wiggle or flick" motion, then stop. This could be mapped to starting or stopping a clip store. Any of the above motions or any detectable intentional motion could be mapped to any desirable operator action or set of actions. Any of the above motions or any detectable intentional motion could be used to start/stop voice control listening. Any of the above motions or any detectable intentional motion could be used to step through a sequence of preset imaging control sets. In combination with some starting action, the motion of the transducer in one axis could be mapped to adjusting the value of a control over a given range. In combination with some starting action, the motion of the transducer in two different axes could be mapped to adjustment of two control values over two given ranges. In combination with some starting action, detection of image change on two axis could be mapped to the movement of an on screen cursor used to interact with on-screen control elements. Moving the transducer in the third axis could be mapped to selections of the control the cursor is over. Further, while the embodiments described above used an ultrasonic handheld imaging transducer, the methods described above may be applied to other types of handheld imaging transducers. Further, other positionable transducers such robotically, or remotely movable transducers may be used. Accordingly, other embodiments are within the scope of the following claims.

In addition to patterns of transducer motion while the transducer is on the patient body, sequences of transducer motion on and off of the body, or motions of the sonographer tapping on the transducer face with a finger or other object may also be used to trigger command signals. When used in this manner, the transducer surface area may be divided into a number of control regions, each region having a different control signal meaning. The length of time of a tap on the transducer face (or head) or the position of the tap on the transducer face (or head) can be used to distinguish different tap types, allowing a binary (or greater) encoding of control signals meanings. For example, two taps on the left end of the transducer followed by one tap on the right can map to selecting a specific exam type. This embodiment allows for the triggering of commands without the sonographer having to remove the transducer from the patient, which would disrupt the exam.

When a sonographer picks the transducer and introduces a finger or palm as a reflective body, the system will interpret this reception, which exceeds a predefined threshold level, as a signal to activate the color. If one desires, one may further elaborate on this kind of binary encoding to include sequences of free-space and solid-body signals into a Morse logic. Furthermore, the transducer surface area may be divided into N regions to simulate an N part touch sensor to enhance its user-interface capabilities.

Table III shows an exemplary two region transducer and some command signals that are map-able to particular motions on the transducer.

TABLE III

| Action | Region 1 | Region 2 | Command Signal |
| --- | --- | --- | --- |
| Lift the transducer | No touch | No touch | System is prepared for command mode |
| Lifted transducer | Touch | No touch | Command 1 |
| Lifted transducer | Touch | Touch | Command 2 |
| Lifted transducer | No touch | Touch | Command 3 |

Another embodiment of employing a transducer as user-interface is the employment of a calibrated passive substrate comprised of a specific map of echo signatures. This substrate can be a strip of material that is placed near the patient or worn by the sonographer in such a way that the movements of the transducer are minimized. A reception of a distinct signature can signify a desired state and trigger a state change, e.g., the start or stop of an ultrasound exam. A transition between distinct signatures by the movement of the transducer over adjacent parts of the substrate can encode parameter quantity changes. The acceleration of this transition may further signify the magnitude of that quantity change. Table IV illustrates an example of scanning a substrate or material other than a patient with a transducer to trigger a command signal or input data.

TABLE IV

| Action | Substrate | Command |
| --- | --- | --- |
| Lift the transducer | No contact | System is prepared for command mode |
| Lifted transducer | Placed on MO substrate | Command 1 (Open Study Utility Page) |
| Lifted transducer | Placed on Network Cable | Command 2 (Output study data to storage media or network) |

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed is:

1. A method for providing an operational command signal to a workstation of an imaging system, said workstation being provided imaging data from a handheld ultrasound transducer that is positionable, comprising:

scanning the handheld ultrasound transducer over a surface of a patient to transmit sound waves to different regions of the patient and to receive in the handheld ultrasound transducer echoes of the transmitted sound waves from the patient, wherein said scanning may result in a scanning motion of the handheld ultrasound transducer;

interrupting said scanning and imparting by hand to the handheld ultrasound transducer a motion, wherein said motion corresponds to one of a plurality of predetermined motion patterns to initiate a corresponding one of a plurality of different operational command signals to the workstation of the imaging system;

discriminating between the scanning motion and said motion imparted to the handheld ultrasound transducer that is intended to initiate an operational command signal;

detecting said motion corresponding to one of the plurality of predetermined motion patterns by comparing a sequence of images formed by the imaging system;

determining from the sequence of images whether there is scanning motion imparted to the handheld ultrasound transducer due to a repositioning of the handheld ultrasound transducer to produce a different image to be displayed by the imaging system or said motion imparted to produce the operational command signal to the workstation; and converting, after the discriminating, the detected one of the plurality of predetermined motion patterns into said operational command signal.

2. The method of claim 1 wherein said detecting uses decimated image data or Doppler tissue.

3. The method of claim 1 wherein said determining includes comparing imparted motion with a level threshold.

4. The method of claim 1 wherein said determining includes comparing imparted motion with a time duration threshold.

5. The method of claim 1 wherein said determining includes comparing imparted motion with an acceleration threshold.

6. The method of claim 1 wherein said motion is imparted by tapping on a face of said handheld ultrasound transducer.

7. The method of claim 6 wherein said face is divided into a number of regions, each of said number of regions corresponding to a distinct map-able control signal.

8. An imaging system comprising:
a workstation;
a transducer for providing imaging data to the workstation, wherein the transducer is a handheld positionable ultrasound transducer;
wherein said workstation responds to operational command signals;
wherein the workstation includes a memory for storing a table mapping predetermined motion patterns with said operational command signals and a processor for detecting a motion imparted by a hand of an operator of the system to the transducer; for discriminating between whether the motion is intended either to perform scanning of a patient or to initiate one of said operational command signals; and then for converting, using the table in the memory, the motion detected to correspond to at least one predetermined motion pattern imparted by the operator of said imaging system to at least one of a predetermined region of interest on a surface of the transducer into the corresponding operational command signal;
wherein the processor is programmed to use said operational command signals to effect predetermined user interface actions to the system;
wherein said detecting comprises comparing a sequence of images formed by the system; and
wherein the processor is programmed to determine from the sequence of images whether to produce a different image to be observed by the operator or imparted to produce the operational command signals to the workstation.

9. The system of claim 8 wherein said determining includes comparing types of motions imparted by the operator.

10. The system of claim 8 wherein said determining includes comparing imparted motion with a level threshold.

11. The system of claim 8 wherein said determining includes comparing imparted motion with a time duration threshold.

12. An imaging system comprising:
a workstation;
a transducer for providing imaging data to the workstation, wherein the transducer is a handheld positionable ultrasound transducer and has deposed within a housing thereof motion sensors;
wherein said workstation responds to operational command signals; and
wherein the workstation includes a memory for storing a table mapping predetermined motion patterns with said operational command signals and a processor for detecting a motion imparted by a hand of an operator of the system to the transducer; for discriminating between whether the motion is intended either to perform scanning of a patient or to initiate one of said operational command signals; and then for converting, using the table in the memory, the motion detected to correspond to at least one predetermined motion pattern imparted by the operator of said imaging system to at least one of a predetermined region of interest on a surface of the transducer into the corresponding operational command signal.

13. A method for providing an operational command signal to a workstation of an ultrasound imaging system comprising:
discriminating between hand motion imparted to the ultrasound imaging transducer intended to initiate an operational command signal and hand motion imparted to the ultrasound imaging transducer during the scanning of a patient; and
converting, after the discriminating, an echo signature of a substrate into said operational command signal, wherein said echo signature is generated upon contact of said substrate with the ultrasound imaging transducer.

14. The method of claim 13 wherein said substrate is worn by a sonographer.

15. The method of claim 1 wherein the hand holding the transducer during the scanning is the same hand used to impart one of a plurality of predetermined plurality of hand motion patterns to initiate a corresponding one of a plurality of different operational command signals to the workstation.

* * * * *